United States Patent [19]

Goi et al.

[11] 4,056,551

[45] Nov. 1, 1977

[54] PREPARATION OF SUCCINYLSUCCINIC ACID DIESTERS

[75] Inventors: Mitsuhiro Goi; Masahiko Miyashita, both of Hirakata, Japan

[73] Assignee: Nippon Gohsei Kagaku Kogyo Kabushiki Kaisha, Osaka, Japan

[21] Appl. No.: 739,284

[22] Filed: Nov. 5, 1976

[30] Foreign Application Priority Data

Nov. 17, 1975 Japan .................................. 50-138432
Nov. 27, 1975 Japan .................................. 50-143094

[51] Int. Cl.$^2$ ...................... C07C 67/30; C07C 69/95
[52] U.S. Cl. ................................................... 560/126
[58] Field of Search ........................... 260/483, 468 K

[56] References Cited

U.S. PATENT DOCUMENTS 3,816,533  11/1974  Brandstrom et al. ............... 260/483

FOREIGN PATENT DOCUMENTS 563,334  5/1974  Switzerland ......................... 260/483

Primary Examiner—Vivian Garner
Attorney, Agent, or Firm—Armstrong, Nikaido & Marmelstein

[57] ABSTRACT

Process for preparing succinylsuccinic acid diesters by subjecting γ-haloacetoacetic acid esters to dimerization in the presence of a base in a mixed medium of alcohol and water containing a specific amount of a water-immiscible organic compound. The succinylsuccinic acid diesters with good quality can be prepared in high yields and can be employed effectively as intermediates for quinacridone pigment.

8 Claims, No Drawings

PREPARATION OF SUCCINYLSUCCINIC ACID DIESTERS

BACKGROUND OF THE INVENTION

The present invention relates to a process for preparing succinylsuccinic acid diesters.

Succinylsuccinic acid diesters are available intermediates for quinacridone pigment. It is known that succinylsuccinic acid diesters are prepared by subjecting γ-haloacetoacetic acid esters to dimerization in a reaction medium in the presence of an inorganic or organic base, and various combination of a reaction medium and a base has been investigated, for instance, (1) dimerization in an alcohol solvent such as ethanol in the presence of an organic base such as sodium ethylate and dimethylamine or an inorganic base such as sodium acetate and ammonia, described in Bull. Soc. Chim. France, 29, 402 (1921), (2) dimerization in an organic solvent having no hydroxyl group such as toluene and dimethyl sulfoxide in the presence of an organic base such as triethylamine and sodium ethylate or an inorganic base such as sodium hydroxide, described in Japanese Patent Disclosure No. 13147/1974, (3) dimerization in water in the presence of sodium ethylate, described in Bull. Soc. Chim. France, 29, 402 (1921), and (4) dimerization in an aqueous buffer solution of an inorganic base, described in Japanese Patent Disclosure No. 47349/1974. However, these known processes have the disadvantages that the yield of succinylsuccinic acid diesters is low and impurities which lower the quality of quinacridone prepared from the diesters are by-produced. For instance, the yield of the above process (1) is at most 29% and the process is not practical. The above process (2) requires an additional recovery step since a large amount of the produced diester is dissolved in the employed organic solvent and the dissolved diester must be recovered from the solvent to raise the yield. In case of the above process (3), the yield is at most 58% and this process is also impractical. In accordance with the above process (4), the diester is prepared in rather high yield, but the trace amount of impurities lowers the quality, especially chroma, of quinacridone prepared from the diester. Purification such as recrystallization to remove the inpurities decreases the yield of the diester due to dissolution of the diester in the mother liquor.

OBJECTS OF THE INVENTION

It is an object of the present invention to provide an improved process for preparing succinylsuccinic acid diesters.

A further object of the invention is to provide a process for preparing pure succinylsuccinic acid diesters in high yields.

These and other objects of the present invention will become apparent from the description hereinafter.

DETAILED DESCRIPTION

It has now been found that the above-mentioned objects can be accomplished by subjecting γ-haloacetoacetic acid esters to dimerization in the presence of a base in a mixed medium of an alcohol and water containing a specific amount of a water-immiscible organic compound.

One of the features of the present invention is to employ a mixture of an alcohol and water as a reaction medium. When an alcohol is employed alone as a reaction medium, the yield of succinylsuccinic acid diester is low. On the other hand, when water is employed alone as a reaction medium, the yield of the diester is low and moreover impurities which lower the quality of quinacridone are by-produced. Also, when a mixture of water and an organic solvent other than the alcohol is employed, the produced succinylsuccinic acid diester is partially dissolved in the medium and an additional step is required to recover the diester dissolved in the medium. The use of the mixture of an alcohol and water is advantageous in providing succinylsuccinic acid diesters having good quality. As the alcohol, any of alcohols are employed in the present invention. Examples of the alcohol are ethanol, n-propanol, isopropanol, n-butanol, isobutanol, sec-butanol, tert-butanol, methoxybutanol, methyl cellosolve, ethyl cellosolve and tetrahydrofurfuryl alcohol. These alcohols may be employed alone or in a mixture thereof. Alcohols having not less than 2 carbon atoms are preferred. Among them, isopropanol is the most preferably employed in point of the yield, cost and boiling point. Also, it is advantageous to employ alcohols being capable of forming an azeotropic mixture with water, such as isopropanol, in that distillation purification of the mixed medium after the completion of the reaction is easy and the resulting distilled azeotropic mixture may be reused as the reaction medium as it is.

The ratio of an alcohol and water may be selected from the range of 1 : 0.1 to 1 : 10 by weight. The alcohol-water mixed medium within the above range sufficiently exhibits the effect of improving the quality of succinylsuccinic acid diesters. Moreover, the ratio of an alcohol and water may be selected in accordance with the kind of the base employed. In case of employing the inorganic base, the ratio of an alcohol and water is suitably employed in a weight ratio of 1 : 1 to 1 : 7, preferably 1 : 1.5 to 1 : 4, since the diesters are prepared in high yield. Also, in case of employing the organic base, the mixing ratio of an alcohol and water is suitably selected from 1 : 0.15 to 1 : 7, preferably 1 : 0.3 to 1 : 4 by weight since the yield of the diester is high. The alcohol-water mixed medium is usually employed in an amount of 200 to 1,000 ml. per mole of the γ-haloacetoacetic acid ester. In the present invention, the amount of alcohol-water mixed medium means the total amount of an alcohol and water which are present in the reaction system. For instance, when the base and γ-haloacetoacetic acid ester are employed in a dissolved or dispersed state in an alcohol or water, the amount of the alcohol-water mixed medium includes such an alcohol or water. By employing the alcohol-water mixed medium as a reaction medium according to the present invention, succinylsuccinic acid diesters having good quality can be obtained as compared with the case of employing an alcohol or water alone. However, the alcohol-water mixed medium alone can not provide high yields.

The other feature of the present invention is to add the specific amount of the water-immiscible organic compound to the reaction medium. The high yields can be obtained by adding the water-immiscible organic compound. Examples of the water-immiscible organic compound employed in the present invention are halogenated aliphatic hydrocarbons such as dichloroethane, carbon tetrachloride, dichloromethane, trichlene and 1,2-dichloropropane, dichloroethylene and aromatic hydrocarbons such as benzene, toluene, chlorobenzene, dichlorobenzene and xylene. Among them, dichloroethane is the most preferably employed in that the high yields can be obtained. The water-immiscible organic compound is usually employed in an amount of 0.5 to 40% by volume based on the total volume of an alcohol and water. When the amount is less than 0.5% by volume, the effect of raising the yield cannot be obtained. On the other hand, when the large amount more than 40% by volume is employed, the yield is lowered rather than raised. Especially, when a large amount of the water-immiscible organic compound is employed in the reaction system using inorganic bases, the effect of raising the yield cannot be remarkably exhibited and, therefore, the water-immiscible organic compound is suitably employed in an amount of 0.5 to 15% by volume, preferably 1 to 10% by volume, based on the total volume of an alcohol and water. In case of employing the organic base as a base, the water-immiscible organic compound is preferably employed in an amount of 0.5 to 30% by volume based on the total volume of an alcohol and water.

The present invention is characterized by the combination of the use of the mixture of alcohol and water as a reaction medium with the addition of the specific amount of the particular water-immiscible organic compound to the above reaction medium. According to the present invention, the γ-haloacetoacetic acid ester, base and water-immiscible organic compound are added to the alcohol-water mixed medium. The base of the γ-haloacetoacetic acid ester may be added in a dissolved or dispersed state in an appropriate solvent. The ester, base and organic solvent may be added to the mixed medium at once, or a part or all of them may be added to the mixed medium continuously or in parts. The dimerization reaction is usually carried out at a temperature of −10° to 20° C., preferably at a temperature of −6° to 2° C. for a period of 10 to 40 hours. After the completion of reaction, the precipitated succinylsuccinic acid diester is separated by filtration or centrifugation to recover the white crystals. Although the thus obtained diester is in a high state of purity and may be employed as an intermediate for quinacridone without purification such as recrystallization, if desired, the purification may be carried out in a conventional manner.

Typical examples of the γ-haloacetoacetic acid ester employed in the present invention are methyl γ-chloroacetoacetate, ethyl γ-chloroacetoacetate, methyl γ-bromoacetoacetate, ethyl γ-bromoacetoacetate, isopropyl γ-chloroacetoacetate and isobutyl γ-chloroacetoacetate.

In the present invention, inorganic bases and organic bases are suitably employed as a base. Examples of the inorganic base employed in the present invention are sodium hydroxide, potassium hydroxide, sodium carbonate, potassium carbonate, sodium hydrogencarbonate and borax. These organic bases may be employed alone or in a mixture thereof. When a mixture of the inorganic bases is employed, suitable mixing ratio varies depending on the kind of the employed inorganic bases as follows:

Sodium carbonate-sodium hydroxide: 0.1–1.5 : 0.1–0.9 by mole
Sodium carbonate-sodium hydrogencarbonate: 0.5–1.5 : 1.5–0.5 by mole
Sodium hydrogencarbonate-sodium hydroxide: 1.0 : 0.2–0.8 by mole
Borax-sodium hydroxide: 1.0 : 0.08–1.5 by mole
Sodium hydroxide-sodium carbonate-sodium hydrogencarbonate: 0.3–0.7 : 0.5–1.5 : 0.3–0.7 by mole Examples of the organic base employed in the present invention are alkali alcoholates such as sodium ethylate, alkali carboxylates such as sodium acetate, monoalkylamines such as monomethylamine, dialkylamines such as diethylamine, and trialkylamines such as trimethylamine, triethylamine, tri-n-propylamine, tri-n-butylamine and tri-n-amylamine. Among these organic bases, the trialkylamines are the most preferably employed. These organic bases may be employed alone or in a mixture thereof. Also, the organic base may be employed in combination with the inorganic base. The inorganic base and organic base are usually employed in an amount of 1.0 to 3.0 moles per mole of the γ-haloacetoacetic acid ester employed. In case of the inorganic base, the amount of 1.1 to 2.0 moles per mole of the ester is preferred. Also, in case of the organic base, the amount is preferably selected from 1.0 to 2.0 moles, more preferably from 1.05 to 1.2 moles, per mole of the γ-haloacetoacetic acid ester.

The present invention is more specifically described and explained by means of the following Examples.

EXAMPLE 1

A 1 liter flask was charged with 150 ml. of a mixed medium consisting of 85% by weight of isopropanol and 15% by weight of water and 30 ml. of dichloroethane, and thereto 100 g. (0.607 mole) of ethyl γ-chloroacetoacetate was added. Further, 55 g. (0.53 mole) of sodium carbonate and 12 g. (0.30 mole) of sodium hydroxide were dissolved in 300 ml. of water and the resulting aqueous solution was added to the flask. The reaction was carried out at a temperature of −3° to −5° C. for 24 hours. After the completion of reaction, the precipitate of the produced diethyl succinylsuccinate was separated by filtration. The separated precipitate was dispersed in 200 ml. of water and was again separated by filtration and washed with water. The amount of the thus obtained diethyl succinylsuccinate was 62.2 g. (yield: 80%). The melting point of the obtained diethyl succinylsuccinate was 127.2° C.

EXAMPLES 2 TO 4 AND COMPARATIVE EXAMPLE 1

The procedures of Example 1 were repeated except that the mixed medium shown in Table 1 was employed instead of the mixed medium employed in Example 1 (Example 2 to 4).

Also, the procedures of Example 1 were repeated except that the mixed medium shown in Table 1 was employed instead of the mixed medium employed in Example 1 and the use of dichloroethane was omitted (Comparative Example 1).

In these Examples and Comparative Example, inorganic base was added in a form of powder.

The results are shown in Table 1.

Table 1

| | Alcohol-water mixed medium | | | Yield of diethyl succinylsuccinate (%) |
|---|---|---|---|---|
| | Alcohol | | Amount of water (g.) | Total amount (ml.) |
| | Kind | Amount (g.) | | | |
| Ex.2 | Isopropanol | 350 | 300 | 737.5 | 72.3 |
| Ex. 3* | Isobutanol | 350 | 300 | 737.5 | 73.7 |
| Ex. 4 | Methyl cellosolve | 400 | 300 | 716.7 | 71.9 |
| Com. | Isopropanol | 350 | 300 | 737.5 | 67.0 |

Table 1-continued

| | Alcohol-water mixed medium | | | Yield of diethyl succinyl-succinate (%) |
|---|---|---|---|---|
| | Alcohol | | Amount of water (g.) | Total amount (ml.) |
| | Kind | Amount (g.) | | |
| Ex. 1 | | | | |

*The reaction was carried out at 0° to 1° C.

EXAMPLES 5 TO 7

The procedures of Example 1 were repeated except that ethyl γ-bromoacetoacetate (Example 5), methyl γ-chloroacetoacetate (Example 6) and isopropyl γ-chloroacetoacetate (Example 7) were employed instead of ethyl γ-chloroacetoacetate, respectively. The corresponding succinylsuccinic acid diesters were obtained in approximately the same yield as in Example 1.

EXAMPLES 8 AND 9

The procedures of Example 1 were repeated except that the inorganic base consisting of 1.5 moles of sodium carbonate and 0.5 mole of sodium hydrogencarbonate (Example 8) and the inorganic base consisting of 0.8 mole of borax and 0.7 mole of sodium hydroxide (Example 9) were employed instead of the inorganic base consisting of 0.53 mole of sodium carbonate and 0.30 mole of sodium hydroxide, respectively.

Diethyl succinylsuccinate was prepared in approximately the same yield as in Example 1.

EXAMPLE 10

The procedures of Example 1 were repeated except that toluene was employed instead of dichloroethane. The yield of diethyl succinylsuccinate was 76.3%.

EXAMPLE 11

The procedures of Example 1 were repeated except that dichloroethane was employed in an amount of 15 ml. instead of 30 ml. The yield of diethyl succinylsuccinate was 78.9%.

COMPARATIVE EXAMPLES 2 AND 3

The procedures of Example 1 were repeated except that dichloroethane was employed in an amount of 0.8 ml. (Comparative Example 2) and 250 ml. (Comparative Example 3), respectively. The yield in Comparative Example 2 was 66.5% and the yield in Comparative Example 3 was 59.0%.

EXAMPLES 12 TO 15

The procedures of Example 1 were repeated except that the water-immiscible organic compound shown in Table 2 was employed instead of dichloroethane.

The results are shown in Table 2.

Table 2

| | Water-immiscible organic compound | Yield (%) |
|---|---|---|
| Ex. 12 | Carbon tetrachloride | 76.8 |
| Ex. 13 | Dichloromethane | 77.2 |
| Ex. 14 | 1,2-Dichloropropane | 76.4 |
| Ex. 15 | Xylene | 75.1 |

EXAMPLE 16 TO 19

The procedures of Example 1 were repeated except that the mixed medium shown in Table 3 was employed instead of the mixed medium employed in Example 1.

The results are shown in Table 3.

Table 3

| | Alcohol-water mixed medium | | | Yield of diethyl succinyl-succinate (%) |
|---|---|---|---|---|
| | Alcohol Kind | Amount (g.) | Amount of water (g.) | Total amount (ml.) |
| Ex. 16 | Isopropanol | 150 | 300 | 487.5 | 79.1 |
| Ex. 17 | Isobutanol | 180 | 300 | 525 | 79.2 |
| Ex. 18 | Methyl cellosolve | 180 | 300 | 487.5 | 78.7 |
| Ex. 19 | n-Propanol | 200 | 300 | 550 | 78.5 |

EXAMPLE 20

A 1 liter flask was charged with 300 ml. of a mixed medium consisting of isopropanol and water in a weight ratio of 1 : 1.4, 50 ml. of dichloroethane, 134 g. (1.33 moles) of triethylamine and 200 g. (1.21 moles) of ethyl γ-chloroacetoacetate. The reaction was carried out at a temperature of −5° to −2° C. for 22 hours. After the completion of reaction, the precipitate of the produced diethyl succinylsuccinate was separated by filtration. After dispersing the separated precipitate into 200 ml. of water, the precipitate was separated again by filtration and was washed with water. The amount of the thus obtained diethyl succinylsuccinate was 130.9 g. (yield: 84.1%). The melting point of the obtained diethyl succinylsuccinate was 127.2° C.

COMPARATIVE EXAMPLE 4

The procedures of Example 20 were repeated except that the use of dichloroethane was omitted. The yield of diethyl succinylsuccinate was 74.1%.

COMPARATIVE EXAMPLES 5 AND 6

The procedures of Example 20 were repeated except that dichloroethane was employed in an amount of 1 ml. (Comparative Example 5) and 150 ml. (Comparative Example 6), respectively. The yield in Comparative Example 5 was 72.9% and the yield in Comparative Example 6 was 63%.

EXAMPLES 21 AND 22

The procedures of Example 20 were repeated except that trimethylamine (Example 21) and triisopropylamine (Example 22) were employed instead of triethylamine, respectively. The yield in Example 21 was 80.1% and the yield in Example 22 was 79.5%.

EXAMPLES 23 TO 26

The procedures of Example 20 were repeated except that the water-immiscible organic compound shown in Table 4 was employed in the amount shown in Table 4 instead of 50 ml. of dichloroethane.

The results are shown in Table 4.

Table 4

| | Water-immiscible organic compound | | Yield of diethyl succinyl-succinate (%) |
|---|---|---|---|
| | Kind | Amount (ml.) | |
| Ex. 23 | Dichloroethane | 30 | 82.0 |
| Ex. 24 | Trichlene | 50 | 82.7 |
| Ex. 25 | Toluene | 50 | 79.8 |
| Ex. 26 | Xylene | 50 | 79.3 |

EXAMPLES 27 TO 29

The procedures of Example 20 were repeated except that the mixed medium shown in Table 5 was employed instead of the mixed medium employed in Example 20.

The results are shown in Table 5.

Table 5

| | Alcohol-water mixed medium | | | Yield of diethyl succinyl-succinate (%) |
|---|---|---|---|---|
| | Alcohol | | Amount of water (g.) | Total amount (ml.) |
| | Kind | Amount (g.) | | |
| Ex.-27 | Isopropanol | 128 | 160 | 320 | 83.1 |
| Ex. 28 | Isobutanol | 100 | 160 | 240 | 79.9 |
| Ex. 29 | Ethanol | 128 | 160 | 320 | 78.0 |

EXAMPLE 30

A 1 liter flask was charged with 300 ml. of a mixed medium consisting of isopropanol and water in a weight ratio of 1 : 0.63, 50 ml. of dichloroethane, 134 g. (1.33 moles) of triethylamine and 200 g. (1.21 moles) of ethyl γ-chloroacetoacetate. The reaction was carried out at a temperature of −5° to −2° C. for 22 hours. After the completion of reaction, the precipitate of the produced diethyl succinylsuccinate was separated by filtration. After dispersing the separated precipitate into 200 ml. of water, the precipitate was separated again by filtration and was washed with water. The amount of the thus obtained diethyl succinylsuccinate was 123.5 g. (yield: 79.5%). The melting point of the obtained diethyl succinylsuccinate was 127.2° C.

EXAMPLES 31 AND 32

The procedures of Example 30 were repeated except that trimethylamine (Example 31) and triisopropylamine (Example 32) were employed instead of triethylamine, respectively. The yield in Example 31 was 78.2% and the yield in Example 32 was 78.0%.

EXAMPLES 33 TO 36

The procedures of Example 30 were repeated except that the water-immiscible organic compound shown in Table 6 was employed in the amount shown in Table 6 instead of 50 ml. of dichloroethane.

The results are shown in Table 6.

Table 6

| | Water-immiscible organic compound | | Yield of diethyl succinylsuccinate (%) |
|---|---|---|---|
| | Kind | Amount (ml.) | |
| Ex. 33 | Dichloroethane | 30 | 77.1 |
| Ex. 34 | Trichlene | 50 | 79.0 |
| Ex. 35 | Xylene | 50 | 75.1 |
| Ex. 36 | Toluene | 50 | 76.2 |

EXAMPLES 37 TO 39

The procedures of Example 20 were repeated except that ethyl γ-bromoacetoacetate (Example 37), methyl γ-chloroacetoacetate (Example 38) and isopropyl γ-chloroacetoacetate (Example 39) were employed instead of ethyl γ-chloroacetoacetate, respectively. The corresponding succinylsuccinic acid diester was prepared in approximately the same yield as in Example 20.

COMPARATIVE EXAMPLES 7 TO 9

Diethyl succinylsuccinate was prepared under the conditions shown in Table 7 in accordance with Example 20.

The results are shown in Table 7.

Table 8

| Com. Ex. No. | Solvent | | Base | | Water-immiscible organic solvent | | Yield of diethyl succinyl-succinate % |
|---|---|---|---|---|---|---|---|
| | Kind | Amount ml. | Kind | Amount mole | Kind | Amount ml. | |
| 7 | Water | 300 | Triethylamine | 1.38 | — | — | 29.5 |
| 8 | Isopropanol | 400 | Triethylamine | 1.30 | — | — | 60.7 |
| 9 | Water-toluene (in a weight ratio of 1 : 0.8) | 400 | Triethylamine | 1.30 | Dichloroethane | 50 | 57.4 |

EXAMPLE 40

The reaction was carried out in the same manner as in Example 1. The resulting crystals of diethyl succinylsuccinate were recovered from the reaction mixture by filtration, and then the obtained mother liquor was distilled to give 141 ml. of a liquid consisting of 84% by weight of isopropanol, 3% by weight of ethanol and 13% by weight of water.

To the thus obtained liquid was further added 9 ml. of a mixture of isopropanol and water in a weight ratio of 85 : 15 to provide a reaction medium. Then, the procedures of Example 1 was repeated again except that 150 ml. of the thus obtained reaction medium was employed instead of 150 ml. of the isopropanol-water mixed medium. The yield of diethyl succinylsuccinate was 79.8%.

EXAMPLE 41

A 1 liter flask was charged with 150 ml. of a mixed medium consisting of 85% by weight of isopropanol and 15% by weight of water, 30 ml. of dichloroethane and 100 g. of ethyl γ-chloroacetoacetate. The reaction was carried out at a temperature of −3° to −5° C. with adding dropwise 34.5 g. of trimethylamine over 3 hours. The reaction was further continued with adding dropwise 10 g. of sodium hydroxide dissolved in 40 ml. of water over 2 hours. After the completion of the reaction, the resulting crystals were filtered, washed and dried. The yield of diethyl succinylsuccinate was 84%.

What we claim is:

1. In the process for preparing a succinylsuccinic acid diester by subjecting a γ-haloacetoacetic acid ester to dimerization in the presence of a base in a reaction medium, the improvement which comprises carrying out the dimerization in a mixed medium of an alcohol having at least 2 carbon atoms and water containing a water-immiscible organic compound selected from the group consisting of halogenated aliphatic hydrocarbons and aromatic hydrocarbons in an amount of 0.5 to 40% by volume based on the total volume of an alcohol and water.

2. The process of claim 1, wherein said alcohol is at least one member selected from the group consisting of ethanol, n-propanol, isopropanol, n-butanol, isobutanol, sec-butanol, tert-butanol, methoxybutanol, methyl cellosolve, ethyl cellosolve and tetrahydrofurfuryl alcohol.

3. The process of claim 1, wherein said mixing ratio of an alcohol and water is selected from 1 : 0.1 to 1 : 10 by weight.

4. The process of claim 1, wherein said water-immiscible organic compound is at least one member selected from the group consisting of dichloroethane, carbon tetrachloride, dichloromethane, trichlene, 1,2-dichloropropane, dichloroethylene, benzene, toluene, chlorobenzene, dichlorobenzene and xylene.

5. The process of claim 1, wherein said base is an inorganic base selected from the group consisting of sodium hydroxide, potassium hydroxide, sodium carbonate, potassium carbonate, sodium hydrogencarbonate and borax.

6. The process of claim 1, wherein said base is at least one member selected from the group consisting of trimethylamine, triethylamine, tri-n-propylamine, tri-n-butylamine and tri-n-amylamine.

7. The process of claim 1, wherein said dimerization is carried out in the presence of an inorganic base in the mixed medium containing the water-immiscible organic compound in an amount of 1 to 10% by volume based on the total volume of an alcohol and water.

8. The process of claim 1, wherein said dimerization is carried out in the presence of a trialkylamine in the mixed medium containing the water-immiscible organic compound in an amount of 0.5 to 30% by volume based on the total volume of an alcohol and water.

* * * * *